(12) United States Patent
Troxler

(10) Patent No.: US 6,635,647 B2
(45) Date of Patent: Oct. 21, 2003

(54) DECAHYDRO-ISOQUINOLINES

(75) Inventor: Thomas J. Troxler, Wahlen (CH)

(73) Assignee: Novartis AG, Basel (CH)

(*) Notice: Subject to any disclaimer, the term of this patent is extended or adjusted under 35 U.S.C. 154(b) by 0 days.

(21) Appl. No.: 10/221,983

(22) PCT Filed: Mar. 21, 2001

(86) PCT No.: PCT/EP01/03211
§ 371 (c)(1),
(2), (4) Date: Sep. 18, 2002

(87) PCT Pub. No.: WO01/70731
PCT Pub. Date: Sep. 27, 2001

(65) Prior Publication Data
US 2003/0120072 A1 Jun. 26, 2003

(30) Foreign Application Priority Data
Mar. 23, 2000 (GB) .............................. 0007108

(51) Int. Cl.[7] ................... A61K 31/496; C07D 401/06; C07D 401/14; C07D 405/14; C07D 413/14
(52) U.S. Cl. ......................... 514/252.16; 514/253.04; 514/253.05; 544/254; 544/263; 544/281; 544/362; 544/363
(58) Field of Search ................. 544/362, 363, 544/254, 263, 281, 253.04, 253.05, 252.16

(56) References Cited
FOREIGN PATENT DOCUMENTS
WO 99/52875 * 10/1999
* cited by examiner Primary Examiner—Emily Bernhardt
(74) Attorney, Agent, or Firm—Joseph J. Borovian

(57) ABSTRACT

The invention provides compounds of formula (I)

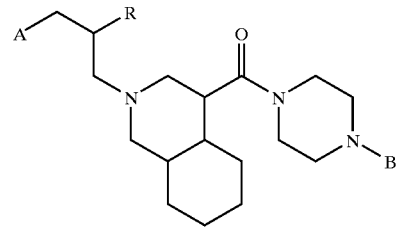

wherein A, B and R are as defined herein and the preparation thereof. The compounds of formula (I) are useful as somatostatin antagonists.

5 Claims, No Drawings

DECAHYDRO-ISOQUINOLINES

The present invention relates to novel decahydro-isoquinoline derivatives, their preparation, their use as pharmaceuticals and pharmaceutical compositions containing them.

More particularly the invention provides a compound of formula I

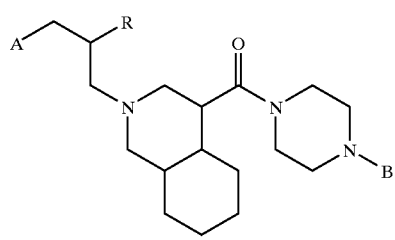

wherein R is hydrogen or $(C_{1-4})$alkyl and A and B, independently, are groups of formula (a), (b), (c), (d) or (e)

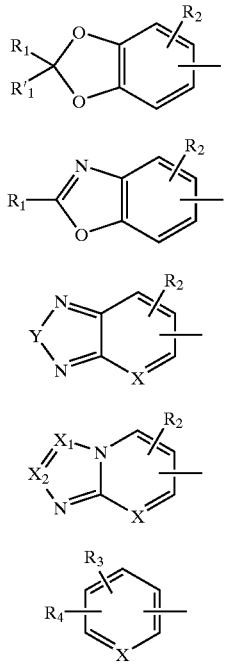

wherein
X, $X_1$ and $X_2$, independently, are —$CR_1$= or —N=
Y is —O—, —S—, —CH=CH— or —NH—
$R_1$ and $R'_1$, independently, are hydrogen, $(C_{1-4})$alkyl or $(C_{1-4})$alkoxy,
$R_2$ is hydrogen, $(C_{1-4})$alkyl, $(C_{1-4})$alkoxy, $(C_{1-4})$alkoxycarbonyl or halogen, and
$R_3$ and $R_4$, independently, are hydrogen, nitro, cyano, trifluoromethyl, $(C_{1-4})$alkyl, $(C_{1-4})$ alkoxy, $(C_{1-4})$ alkoxycarbonyl or $(C_{1-4})$alkanoyl,
in free base or acid addition salt form.

On account of the asymmetrical carbon atoms which are present in the compounds of formula I and their salts, the compounds may appear in optically active form or in form of mixtures of optical isomers, e.g. in form of racemic mixtures. All optical isomers and their mixtures including the racemic mixtures are part of the present invention.

Halogen is fluorine, chlorine, bromine or iodine, preferably fluorine or chlorine. The above-defined alkyl and alkoxy groups preferably represent methyl and methoxy.

In a further aspect, the invention provides a process for the production of the compounds of formula I and their salts, whereby a compound of formula II

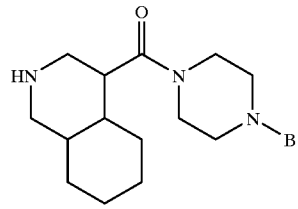

wherein B is as defined above, is reacted with a compound of formula III

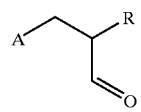

wherein A and R are as defined above, and the compounds of formula I thus obtained are recovered in free base or acid addition salt form.

The reaction can be effected according to known amine formation methods.

Working up the reaction mixtures according to the above process and purification of the compounds thus obtained may be carried out in accordance to known procedures.

Acid addition salts may be produced from the free bases in known manner and vice-versa The compounds of formula II may be produced from known compounds using conventional procedures, for example by amidation of a compound of formula IV

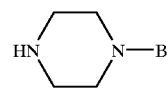

wherein B is as defined above, with tert.-butoxycarbonyl-octahydro-isoquinoline-4-carboxylic acid, which can be prepared from isoquinoline-4-carboxylic acid ethyl ester, e.g. as described in Example 1, steps b) to e).

The compounds of formula III may be produced in conventional manner from compounds of formula V

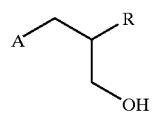

wherein A and R are as defined above, e.g. as described in Example 1, steps h) and i).

The compounds of formula V may be produced in conventional manner, e.g. from compounds of formulae VI and VII

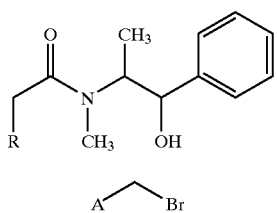

wherein A and R are as defined above, as described in Example 1, steps f) and g) or from compounds of formulae VIII and IX

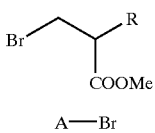

wherein A and R are as defined above. A resulting compound of formula V may be converted into another compound of formula V e.g. as described in Example 1, step h).

The starting compounds of formulae IV, VI and VII are known or may be produced in analogous manner to known compounds.

Compounds of formula I and their pharmaceutically acceptable acid addition salts, hereinafter referred to as agents of the invention, exhibit valuable pharmacological properties when tested in vitro using somatostatin (somatotropin release inhibiting factor, SRIF) receptor expressing cell cultures and in animals, and are therefore useful as pharmaceuticals.

In particular the agents of the invention show high affinity to somatostatin receptors. More particularly they are selective antagonists at Somatostatin $sst_3$ receptors, previously called SSTR-3 receptors (see Hoyer et al., TIPS, 1995, 16; 86–88), as determined in radioligand binding and second messenger studies [see for example K. Kaupmain et al., FEBS LETTERS 1993, 331: 53–59, S. Siehler et al. Naunyn Schmiedeberg's Arch Pharmacol, 1999, 360: 488–499] where they exhibit selective affinity for $sst_3$ receptors with pKd values between about 7.5 and 9.0.

The agents of the invention are therefore useful for treatment in anxiety, depression, social phobia, panic disorders, post traumatic stress disorders, ADHD (attention deficit and hyperactivity disorders), bipolar disorders, schizophrenia, including negative symptoms, neurodegenerative diseases such as learning/memory disorders, dementia, age associated memory impairment, SDAT, for the treatment of tumours and for vascular disorders and immunological diseases, as confirm in a range of standard tests as indicated below:

At doses of about 0.3 to 3 mg/kg p.o., the agents of the invention increase exploratory behaviour of mice in the open half of the half enclosed platform, a model which is predictable for anxiolytic activity (Psychopharmacology, 1986, 89:31–37).

In the same half enclosed platform model, the agents of the invention at the above indicated doses also increase vigilance of the mice. The compounds are therefore indicated for the treatment of depression, schizophrenia and dementia, in particular of senile dementia of the Alzheimer type (SDAT).

In the intruder mouse test [Triangle, 1982, 21: 95–105; J. Clin. Psychiatry, 1994, 55:9 (suppl. B) 4–7], the agents of the invention increase social investigation and reduce defensive ambivalence in the treated intruder mouse at doses of about 1 to about 10 mg/kg s.c., suggesting an antimanic profile like carbamazepine and lithium, a neuroleptic profile like clozapine and an anxiolytic profile like diazepam.

In the stress-induced hyperthermia- and the elevated plus-maze paradigm in mice [Lecci et al., Psychopharmacology 101:255–261 (1990) and Rodgers R. J. Behav. Pharmacol. 8: 477–496 (1998), respectively] the agents of the invention reduced the increase in body-temperature and increased the time spent on the open arms, respectively. They are therefore indicated for the treatment of anxiety disorders and panic disorders.

Futhermore at said doses the agents of the invention (given acutely) increase aggressive behaviour (attacks, chases, bites) in the Matched Pairs Situation test in mice [Dixon et al., J. Clin. Psychiatry 55: (9) [Suppl. B] 4–7 (1994)]. Since as mentioned above they additionally attenuate defensive behaviours in the intruder mouse test, the agents of the invention exhibit an ethopharmacological profile which is very similar to that of clozapine and to some extent to that of antimanic agents (Lithium, carbamazepine, valproate). They are therefore indicated for the treatment of affective disorders including bipolar disorders e.g. manic-depressive psychoses, extreme psychotic states e.g. mania, schizophrenia, and excessive mood swings where behavioural stabilisation is desired. In addition, the compounds are indicated in anxiety states, generalised anxiety as well as social stress and agoraphobia, as well as those behavioural states characterised by social withdrawal e.g. negative symptoms [Dixon AK Brit.J.Med.Psychol. 71:,417–445, Dixon AK Fisch HU Neuroscience and Biobehavioural Reviews. 23 (1990) 345–358] and post traumatic stress disorders.

Moreover when given at doses of about 0.03 to 3 mg/kg p.o. to rodents, the agents of the invention counteract electroshock-induced amnesia, increase retention performance in a passive avoidance paradigm (Mondadori et. al., Pharmacology Communications 1992, 2: 93–97) and improve social recoin (Mondadori et al., Behavioural Brain Research 1996, 77: 227–229). The compounds are therefore indicated for the tent of cognitive disturbances and learning/memory disorders.

The positive effects on memory acquisition/retention combined with the sociotropic components displayed by the agents of the invention, suggest that these will prove useful in the treatment of ADHD and various types of dementias, including Alzheimer's disease.

The agents of the invention are also effective in the treatment of various kinds of tumours, particularly of $sst_3$ receptor bearing tumours, as indicated in proliferation tests with various different cancer cell lines and in tumour growth experiments in nude mice with hormone dependent tumours [see for example: G. Weckbecker et al., Cancer Research 1994, 54: 6334–6337]. Thus, the compounds are indicated in the treatment of, for example, cancers of the breast, the prostate, the colon, the pancreas, the brain and the lung (small cell lung cancer) and for in vivo imaging of sst3 receptor bearing tumours.

For all the above mentioned indications, the appropriate dosage will of course vary depending upon, for example, the compound employed, the host, the mode of administration and the nature and severity of the condition being treated. However, in general satisfactory results in animals are indicated to be obtained at a daily dosage of from about 0.1 to about 10 mg/kg animal body weight. In larger mammals, for example h an indicated daily dosage is in the range from about 5 to about 200 mg, preferably about 10 to about 100 mg of the compound conveniently administered in divided doses up to 4 times a day or in sustained release form.

The agents of the invention may be administered in free form or in pharmaceutically acceptable salt form. Such salts may be prepared in conventional manner and exhibit the same order of activity as the free compounds.

Accordingly in a further aspect the present invention provides the agents of the invention for use as pharmaceuticals, more specifically for treatment in the above-mentioned conditions, e.g. schizophrenia, depression, anxiety and bipolar disorders.

The present invention furthermore provides a pharmaceutical composition comprising an agent of the invention in association with at least one pharmaceutically acceptable diluent or carrier. Such compositions may be formulated in conventional manner. Unit dosage forms contain, for example, from about 0.25 to about 50 mg of an agent according to the invention.

Agents of the invention may be administered by any conventional route, for example parenterally e.g. in form of injectable solutions or suspensions, or enterally, preferably orally, e.g. in the form of tablets or capsules.

The preferred indications are schizophrenia (especially negative symptoms and cognitive impairment), depression, anxiety and affective disorders, including bipolar disorders, e.g. mania.

The preferred compound is the compound of example 32. With reference to the above-mentioned tests, in the intruder mouse this compound at doses of 0.3, 1 and 3 mg/kg p.o. increases attention and social exploration and reduces defensive ambivalence and arrested flight. In the social recognition test it increases memory at doses of 0.03 to 30 mg/kg p.o. It also reduces stress-induced hypothermia in mice at doses of 0.3 to 10 mg/kg p.o.

In accordance with the foregoing, the present invention also provides the use of an agent of the invention as a pharmaceutical, e.g. for the treatment of schizophrenia, depression, anxiety and bipolar disorders.

Moreover the present invention provides the use of an agent of the invention for the manufacture of a medicament for the treatment of any condition mentioned above, e.g. schizophrenia, depression, anxiety and affective disorders.

In still a further aspect the present invention provides a method for the treatment of any condition mentioned above, e.g. schizophrenia, depression, anxiety and bipolar disorders, in a subject in need of such treatment, which comprises administering to such subject a therapeutically effective amount of an agent of the invention.

The following examples illustrate the invention. The tends are given in degrees Celsius and are uncorrected.

EXAMPLE 1

[4-(3,4-Difluoro-phenyl)-piperazin-1-yl]-[(4S,4aS, 8aR)-2-(2-(S)-methyl-3-quinoxalin-6-yl-propyl)-decahydro-isoquinolin-4-yl]-methanone a) Isoquinoline-4-carboxylic Acid Ethyl Ester Prepared from 4-bromo-isoquinoline according to R. A. Head et al., Tetrahedron Letters 1984, 25(51), 5939, via Pd(0) catalysed carbonylation.

b) (+/−)-(4S,4aS,8aR)-Decahydro-isoquinoline-4-carboxylic Acid Ethyl Ester

Isoquinoline4-carboxylic acid ethyl ester (85.7 g, 0.426 mol) is dissolved in HOAc (1000 ml) and hydrogenated at 150 bar and 60° for 2 h in the presence of 5% Rh/C (86 g). The mixture is filtered and the filtrate evaporated. The residue is dissolved in MTBE (500 ml) and washed with 2N $KHCO_3$ (400 ml) and brine (100 ml). The combined water phases are exhaustively extracted with DCM (3×150 ml), the extracts dried over $Na_2SO_4$ and evaporated to yield the crude acetate salt of the desired product. Recrystallization from $DCM/Et_2O$ yields the pure acetate salt. This salt is dissolved in water (200 ml) and cooled to 0°. Cold 2N NaOH (150 ml) is slowly added and the mixture extracted with DCM (1×250 ml, 2×150 ml, 1×100 ml). The extracts are dried ($Na_2SO_4$) and evaporated. The residue is crystallised from 300 ml hexanes at −20° to yield the pure product as a white crystal powder, m.p. 44°–52°. TLC (silicagel, $EtOAc/MeOH/NH_4OH$ 85:15:1): rf 0.25. Two further portions can be crystallised from the mother liquor with somewhat lower melting points (42°–52° and 38°–51°).

c) (4S,4aS,8aR)-Decahydro-isoquinoline-4-carboxylic Acid Ethyl Ester

Racemic decahydro-isoquinoline4carboxylic acid ethyl ester (13.67 g) is dissolved in EtOH (70 ml) and added to a solution of [−]-di-O,O'p-toluoyl-L-tartaric acid in abs. EtOH (70 ml). The mixture is left for crystallisation at room temperature for 3 days, then filtered and the solid washed with cold EtOH and $Et_2O$ and dried in vacuo. White plates of tartrate, m.p. 184°–187°, are obtained. Recrystallization from EtOH (85 ml) yields pure salt, m.p. 184–188°. This tartrate is dissolved in water (50 ml), 25% $NH_4OH$ (1.5 ml) and 2N $K_2CO_3$ (25 ml) and vigorously stirred with DCM (50 ml) for 15 min. The phases are separated, the aqueous phase extracted with DCM (2×25 ml) and the combined organic phases dried ($Na_2SO_4$) and evaporated. The free base is obtained as a colorless oil, dissolved in warm hexane (30 ml), filtered and slowly cooled to −20°. Standing over night at −20°, filtering, washing with cold hexane and drying afford a white solid m.p. 59.5°–61.5°. A second crop is obtained from the mother liquor. ee>99% (capillary electrophoresis with chiral stationary phase). $[\alpha]_D^{20}$=−2.8° (c=1, EtOH). The absolute configuration is proven to be (4S,4aS, 8aR) via NOE NMR experiments on a moshers acid amide and x-ray crystallography on the same derivative.

d) (4S,4aS,8aR)-tert.-Butoxycarbonyl-decahydro-isoquinoline-4-carboxylic Acid

A solution of (4S,4aS,8aR)-decahydro-isoquinoline-4carboxylic acid ethyl ester (21.13 g, 0.1 mol) in EtOH abs (200 ml) is cooled to 0°. A solution of $Boc_2O$ (24 g, 0.11 mol) in EtOH (50 ml) is added dropwise over 20 minutes and the solution stirred at room temperature for 2 h. Approximately 65 ml EtOH are distilled off under reduced pressure. 1 N LiOH (140 ml, 0.14 mol) is added and the mixture stirred at room temperature for 3 days. Most of the solvent is distilled off under reduced pressure, brine (250 ml) is added, the solution extracted with MTBE (100 ml) and the organic extract reextracted with brine (2×10 ml). The combined brine phases are acidified with 2N HOAc (75 ml) and then extracted with DCM (1×250 ml, 1×100 ml, 1×50 ml). Drying of the combined extracts ($Na_2SO_4$), evaporation of the solvent and recrystallization from hexanes (250 ml) at −20° afford the desired acid as white short needles, m.p. 112–118°. TLC (silicagel, $DCM/MeOH/NH_4OH$ 85:15:1): rf 0.32.

e) (4S,4aS,8aR)-Decahydro-isoquinolin-4-yl)-[4-(3,4-difluoro-phenyl)-piperazin-1-yl]-methanone A solution of (4S,4aS,8aR)-tert.-butoxycarbonyl-octahydro-isoquinoline4-carboxylic acid (10.78 g, 38 mmol) in DCM (200 ml) is cooled to −75°. Hexachloroacetone (5.44 g, 19.93 mmol) is added, followed by a solution of 1,2-bis(diphenylphosphino)-ethane (7.97 g, 20 mmol) in DCM (100 ml), dropwise over 45 minutes. The mixture is stirred for 1 h at −75° and then treated with a solution of 4-(3,4-difluoro-phenyl)-piperazin (7.92 g, 39.95 mmol) and Et₃N (4.04 g, 40 mmol) in DCM (60 ml), dropwise over 30 minutes. The mixture is stirred for 1 h at room temperature and then evaporated to dryness. The residue is suspended in MTBE (300 ml), cooled to 0° for 30 min. and filtered. Evaporation of the filtrate afford the crude coupling product as a brown oil. It is dissolved in DCM (130 ml), cooled to 0° and slowly treated with trifluoroacetic acid (44 ml). After stirring for 1 h at room temperature, DCM (130 ml) is added and 1M NaHCO₃ (570 ml) is added dropwise at 0°. The phases are separated, the organic phase dried (Na₂SO₄) and evaporated to a volume of about 50 ml. Et₂O (100 ml) is added and the mixture left for crystallisation over night at 5°. Filtration and drying in vacuo afford the desired product as slightly brownish short needles, m.p. 190–199°. TLC (silicagel, DCM/MeOH/NH₄OH 85:15:1): rf 0.18.

f) (S)-3-Benzo[1,2,5]thiadiazol-5-yl-N-[(1R,2R)-2-hydroxy-1-methyl-2-phenyl-ethyl]-2,N-dimethyl-propionamide Water free LiCl (59.4 g, 1.4 mol) is carefully dried in vacuo at 600° for 10 minutes and then the vessel purged with Ar. THF (460 ml) is added and cooled to 0°. A solution of LDA (2M in THF/heptane/Et₂O, 200 ml, 0.4 mol) is added and cooled to −75°. A solution of N-[(1R,2R)-2-hydroxy-1-methyl-2-phenyl-ethyl]-N-methyl-propionamide (44.4 g, 0.2 mol) in 460 ml THF is added dropwise over 170 minutes while maintaining the internal temperature at −62° to −69°. After stirring for 1 h at −75°, the cooling bath is removed for 30 minutes, during which time the temperature rises to −30°. The mixture is recooled to −75° and then treated with a solution of 5-bromomethyl-benzo[1,2,5]thiadiazole (34.8 g, 0.152 mol) in 260 ml THF during 85 min at −70° to −78°. The mixture is then stirred for 40 h at −78°. A 15% NH₄Cl solution (1000 ml) is added and the mixture stirred well. Extraction with EtOAc (2×500 ml), drying (Na₂SO₄) and evaporation afford crude product. MPLC purification (2 kg silicagel, EtOAc/hexanes 2/1) afford pure product as a orange oil. Diastereomeric ration 92:8 (NMR, 120°). TLC (silicagel, EtOAc/hexanes2:1): rf 0.38.

g) (S)-3-Benzo[1,2,5]thiadizol-5-yl-2-methyl-propan-1-ol

A solution of 2M LDA in THF/heptane/Et₂O (147 ml, 0.294 mol) is diluted with 415 ml THF and cooled to 0°. At 5° to 10°, BH₃.NH₃ (10.05 g, 0.293 mol) is added portionwise. The solution is stirred at 0° for 15 minutes, at room temperature for 15 minutes and then recooled to 0°. Then, a solution of (S)-3-benzo[1,2,5]thiadiazol-5-yl-N-[(1R,2R)-2-hydroxy-1-methyl-2-phenyl-ethyl]-2,N-dimethyl-propionamide (27.2 g, 0.0736 mol) in THF (120 ml) is added dropwise over 30 minutes. The dark red solution is stirred at 0° for 3 h. 2 N HCl (700 ml) is added at 0° and the mixture stirred at this temperature for 30 minutes. Extraction with EtOAc (400 ml and 200 ml), washing of the organic phases with brine, drying with Na₂SO₄ and evaporation afford the crude product as a yellow-brown oil. MPLC purification (silicagel, 1 kg, EtOAc/hexane 2:1) yield pure (S)-3-Benzo[1,2,5]thiadiazol-5-yl-2-methyl-propan-1-ol as a yellow oil. ee=93.3% (HPLC on chiral stat. phase). TLC (silicagel, EtOAc/hexanes 2:1): rf 0.6.

h) (S)-2-Methyl-3-quinoxalin-6-yl-propan-1-ol

A solution of (S)-3-benzo[1,2,5]thiadiazol-5-yl-2-methyl-propan-1-ol (5 g, 24 mmol) in EtOH (60 ml) is cooled to 0° and then treated with half concentrated HCl (40 ml, ca. 200 mmol). Zn dust (8.5 g, 130 mmol) is added in 1 g portions at 0°, one portion every 5 minutes. After the last addition, the mixture is stirred at 10° to 15° for 45 minutes. Under ice cooling, half concentrated NH₄OH (40 ml, ca. 290 mmol) is added dropwise. The mixture is filtered over Hyflo, the filtrate concentrated under reduced pressure and the remaining aqueous phase twice extracted with EtOAc (150 ml, 50 ml). Drying over Na₂SO₄ and evaporation give the diamnino intermediate as a brownish, clear oil which tends to darken upon exposure to light and air. This intermediate is dissolved in absolute EtOH (60 ml) and cooled to 0°. 1,4dioxane-2,3-diol (3.75 g, 31.2 mmol) is added at once and the solution stirred at room temperature for 2 h. The mixture is evaporated to dryness, the residue distributed between brine (50 ml) and DCM (50 ml), the organic phase washed with brine (25 ml), dried over Na₂SO₄ and evaporated to afford (S)-2-methyl-3-quinoxalin-6-yl-propan-1-ol as a brownish, clear, viscous oil of sufficient purity for the next step. ee=91% (HPLC on chiral stat. phase). TLC (silicagel, DCM/MeOH/NH₄OH 85:15:1): rf 0.68.

i) (S)-2-Methyl-3-quinoxalin-6-yl-propionaldehyde

A solution of crude (S)-2-methyl-3-quinoxalin-6-yl-propan-1-ol (3.68 g, 18.19 mmol) in toluene (37 ml) is treated with TEMPO (28.4 mg, 0.152 mmol) and KBr (216.5 mg, 1.82 mmol) in 0.9 ml water. 37 ml of a 0.5 M sodiumhypochlorite solution of pH 8–9 (prepared by mixing 34 ml 0.75 M sodiumhypochlorite solution with 16 ml water and 0.85 g NaHCO₃) is added dropwise over 20 minutes at 5° to 8°. After 5 minutes stifling at 0°, the two phase mixture is filtered over Hyflo, the phases separated, the organic phase washed with a solution of 116 mg KI in 15 ml 1 N HCl, then 15 ml of a 5% Na₂S₂O₃ solution and finally 15 ml brine. Drying over Na₂SO₄ and evaporation afford crude aldehyde. MPLC purification (silicagel, EtOAc/hexane 2:1) yield pure (S)-2-Methyl-3-quinoxalin-6-yl-propionaldehyde as a slightly yellow clear oil. TLC (silicagel, EtOAc/hexanes 2:1): rf 0.37.

j) [4-(3,4-Difluoro-phenyl)-piperazin-1-yl]-[(4S,4aS,8aR)-2-(2(S)-methyl-3-quinoxalin-6-yl-propyl)-decahydro-isoquinolin-4-yl]-methanone To a solution of (S)-2-methyl-3-quinoxalin-6-yl-propionaldehyde (2.7 g, 13.48 mmol) in dichloroethane (100 ml) is added (4S,4aS,8aR)-decahydro-isoquinolin-4-yl)-[4-(3,4-difluoro-phenyl)-piperazin-1-yl]-methanone (5.36 g, 11.22 mmol) and stirred for 5 minutes. NaBH(OAc)₃ (3.56 g, 16.8 mmol) is added and the mixture stirred for 1 h. A 1 M solution of NaHCO₃ (100 ml) is added and intensively stirred for 15 minutes. The phases are separated, the organic phase dried over Na₂SO₄ and evaporated to afford 7.2 g of the crude product. MPLC purification (silicagel, EtOAc, then EtOAc/MeOH 5:1) yield pure [4-(3,4-Difluoro-phenyl)-piperazin-1-yl]-[(4S,4aS,8aR)-2-(2(S)-methyl-3-quinoxalin-6-yl-propyl)-decahydro-isoquinolin-4-yl]-methanone. This base is dissolved in 60 ml warm MeOH and treated with maleic acid (1.3 g, 11.22 mmol) in 20 ml MeOH. The solution is diluted with Et₂O (450 ml), and the slightly cloudy solution filtered through Hyflo. Crystallisation first at room temperature and then at 5° afford the maleic acid salt, m.p. 1200–1230. Recrystallization from 50 ml MeOH and 100 ml Et₂O yield the pure maleic acid salt, m.p. 129°–131°.

The following compounds are prepared analogously to Example 1:

| Expl. | A | R | B | Core | M.p. |
|---|---|---|---|---|---|
| 2 | Benzo[1,3]dioxol-5-yl | (R,S)-Me | 4-Nitro-phenyl | (+/−) | 70–75° |
| 3 | Benzo[1,3]dioxol-5-yl | (R,S)-Me | 1-Methyl-6-oxo-1,6-dihydro-pyridin-2-yl | (+/−) | 78–83° |
| 4 | Benzo[1,3]dioxol-5-yl | (R,S)-Me | Imidazo[1,2-b]pyridazin-6-yl- | (+/−) | 70–75° |
| 5 | Benzo[1,3]dioxol-5-yl | H | 4-Nitro-phenyl | (+/−) | 74–78° |
| 6 | Benzo[1,3]dioxol-5-yl | H | 3,4-Difluoro-phenyl | (−) | 42–45° |
| 7 | Benzo[1,3]dioxol-5-yl | (S)-Me | 3,4-Difluoro-phenyl | (−) | 115–120°* |
| 8 | Benzo[1,3]dioxol-5-yl | (S)-Me | Benzo[1,2,5]oxadiazol-5-yl | (−) | 133–135°* |
| 9 | Benzo[1,3]dioxol-5-yl | (S)-i-Pr | 3,4-Difluoro-phenyl | (−) | 46–50° |
| 10 | Benzo[1,3]dioxol-5-yl | (S)-i-Pr | Benzo[1,2,5]oxadiazol-5-yl | (−) | 40–45° |
| 11 | 4-Methoxycarbonyl-benzo[1,3]dioxol-6-yl | (R,S)-Me | 3,4-Difluoro-phenyl | (+/−) | 60–65° |
| 12 | 2,2-Difluoro-benzo[1,3]dioxol-5-yl | (R,S)-Me | 3,4-Difluoro-phenyl | (+/−) | 43–46° |
| 13 | 4-Fluoro-phenyl | (R,S)-Me | 4-Nitro-phenyl | (+/−) | 95–100°** |
| 14 | 4-Fluoro-2-methyl-phenyl | (R,S)-Me | 4-Nitro-phenyl | (+/−) | 70–75° |
| 15 | Benzo[1,2,5]oxadiazol-5-yl | (R,S)-Me | 3,4-Difluoro-phenyl | (+/−) | 56–61° |
| 16 | Benzo[1,2,5]thiadiazol-5-yl | H | 3,4-Difluoro-phenyl | (−) | 45–48° |
| 17 | Benzo[1,2,5]thiadiazol-5-yl | (R,S)-Me | 3,4-Difluoro-phenyl | (+/−) | 60–64° |
| 18 | Benzo[1,2,5]thiadiazol-5-yl | (S)-Me | 3,4-Difluoro-phenyl | (−) | 151–155°* |
| 19 | Benzo[1,2,5]thiadiazol-5-yl | (S)-Me | Benzo[1,2,5]oxadiazol-5-yl | (−) | 88–92° |
| 20 | Quinoxalyl-6-yl | (S)-Me | Benzo[1,2,5]oxadiazol-5-yl | (−) | 75–80° |
| 21 | 3,5-Diacetyl-phenyl | (R,S)-Me | 3,4-Difluoro-phenyl | (+/−) | 61–66° |
| 22 | 3,5-Diacetyl-phenyl | H | 3,4-Difluoro-phenyl | (−) | 67–70° |
| 23 | 3,5-Diacetyl-phenyl | H | Benzo[1,2,5]oxadiazol-5-yl | (−) | 80–83° |
| 24 | 3,5-Dimethoxy-carbonyl-phenyl | (R,S)-Me | 4-Nitro-phenyl | (+/−) | 185–190° |
| 25 | 3,5-Dimethoxy-carbonyl-phenyl | (R,S)-Me | 3,4-Difluoro-phenyl | (+/−) | 129–135° |
| 26 | 3,5-Dimethoxy-carbonyl-phenyl | (R,S)-Me | Benzo[1,2,5]oxadiazol-5-yl | (+/−) | 230–234°** |
| 27 | 3,5-Dimethoxy-carbonyl-phenyl | H | 4-Nitro-phenyl | (−) | 85–90° |
| 28 | 3,5-Dimethoxy-carbonyl-phenyl | (R,S)-Me | 4-Nitro-phenyl | (+) | 82–87° |
| 29 | 3,5-Dimethoxy-carbonyl-phenyl | (R,S)-Me | 4-Nitro-phenyl | (−) | 84–89 |
| 30 | Benzo[1,3]dioxol-5-yl | (S)-Me | [1,2,5]Oxadiazolo[3,4-.b.]pyridin-5-yl | (−) | 78–83° |
| 31 | Quinoxalin-6-yl | (S)-Me | [1,2,5]Oxadiazolo[3,4-.b.]pyridin-5-yl | (−) | 80–85° |
| 32 | 6-Methoxy-pyridin-3-yl | (S)-Me | 3,4-Difluoro-phenyl | (−) | 40–45° 113–115°* |
| 33 | Benzooxazol-5-yl | (R)-Me | 3,4-Difluoro-phenyl | (−) | 55–60° |
| 34 | Benzooxazol-5-yl | (S)-Me | 3,4-Difluoro-phenyl | (−) | 57–63° |
| 35 | Benzooxazol-5-yl | (R)-Me | Benzo[1,2,5]oxadiazol-5-yl | (−) | 65–70° |
| 36 | Benzo[1,3]dioxol-5-yl | (S)-Me | 4-Cyano-phenyl | (−) | 119–135° |
| 37 | Benzo[1,2,5]thiadiazol-5-yl | (S)-Me | 4-Cyano-phenyl | (−) | 116–127° |
| 38 | Quinoxalin-6-yl | (S)-Me | 4-Cyano-phenyl | (−) | 110–130° |
| 39 | Benzo[1,2,5]thiadiazol-5-yl | (S)-Me | (5-Cyano-pyridin-2-yl) | (−) | 154–166 |
| 40 | [1,2,4]Triazolo[1,5-.a.]pyridin-6-yl | (R,S)-Me | 3,4-Difluoro-phenyl | (−) | 62–64° |
| 41 | Imidazo[1,2-.a.]pyridin-6-yl | (R,S)-Me | 3,4-Difluoro-phenyl | (−) | 70–75° |
| 42 | 5-Methoxy-pyridin-3-yl | (R,S)-Me | 3,4-Difluoro-phenyl | (−) | 36–39° |
| 43 | 6-Fluoro-pyridin-3-yl | (R,S)-Me | 3,4-Difluoro-phenyl | (−) | 39–42° |
| 44 | 2-Methyl-benzooxazol-5-yl | (S)-Me | 3,4-Difluoro-phenyl | (−) | 58–62° |
| 45 | [1,2,4]Triazolo[1,5-.a.]pyridin-6-yl | (R)-Me | 3,4-Difluoro-phenyl | (−) | 63–66° |
| 46 | 6-Methoxy-pyridin-3-yl | (R)-Me | 3,4-Difluoro-phenyl | (−) | 45–48° |
| 47 | 2-Methyl-benzooxazol-5-yl | H | 3,4-Difluoro-phenyl | (−) | 40–43° |
| 48 | Imidazo[1,2-.a.]pyridin-6-yl | (S)-Me | Benzo[1,2,5]oxadiazol-5-yl | (−) | 79–81° |
| 49 | 6-Methoxy-pyridin-3-yl | (S)-Me | Benzo[1,2,5]oxadiazol-5-yl | (−) | 60–65° |

-continued

| Expl. | A | R | B | Core | M.p. |
|---|---|---|---|---|---|
| 50 | 6-Methoxy-pyridin-3-yl | (S)-Me | 4-Cyano-phenyl | (−) | 75–80° |
| 51 | 2-Methyl-benzooxazol-5-yl | (S)-Me | Benzo[1,2,5]oxadiazol-5-yl | (−) | 79–84° |
| 52 | 2-Methyl-benzooxazol-5-yl | (S)-Me | 4-Cyano-phenyl | (−) | 77–82° |
| 53 | 6-Ethoxy-pyridin-3-yl | (S)-Me | 3,4-Difluoro-phenyl | (−) | 44–47° |
| 54 | 6-Ethoxy-pyridin-3-yl | (S)-Me | 4-Cyano-phenyl | (−) | 60–65° |
| 55 | 6-Ethoxy-pyridin-3-yl | (S)-Me | 3,4-Difluoro-phenyl | (−) | 57–63° |
| 56 | 6-Ethylamino-pyridin-3-yl | (S)-Me | 3,4-Difluoro-phenyl | (−) | 55–60° |
| 57 | 2-Methyl-[1,2,4]triazolo[1,5-a.]pyridin-6-yl | (S)-Me | 3,4-Difluoro-phenyl | (−) | 136–139°* |
| 58 | 2-Methyl-imidazo[1,2-a.]pyridin-6-yl | (S)-Me | 3,4-Difluoro-phenyl | (−) | 46–48° |
| 59 | 2-Methyl-benzothiazol-5-yl | (R,S)-Me | 3,4-Difluoro-phenyl | (−) | 64–68° |
| 60 | 6-Methoxy-pyridin-3-yl | (R)-Me | 3,4-Difluoro-phenyl | (−) | 116–120°* |
| 61 | 6-Methylamino-pyridin-3-yl | (R,S)-Me | 3,4-Difluoro-phenyl | (−) | 65–70° |
| 62 | 2-Ethyl-benzooxazol-5-yl | (R,S)-Me | 3,4-Difluoro-phenyl | (−) | 53–58° |
| 63 | 2-Isopropyl-benzooxazol-5-yl | (R,S)-Me | 3,4-Difuoro-phenyl | (−) | 60–63° |
| 64 | 2-Methoxy-benzooxazol-5-yl | (R,S)-Me | 3,4-Difluoro-phenyl | (−) | 74–80° |
| 65 | 2-Methyl-benzooxazol-6-yl | (R,S)-Me | 3,4-Difluoro-phenyl | (−) | 58–62° |
| 66 | 2,2-Dimethyl-benzo[1,3]dioxol-5-yl | (R,S)-Me | 3,4-Difluoro-phenyl | (−) | 60–64° |
| 67 | 2,3-Dihydro-benzo[1,4]dioxin-6-yl | (R,S)-Me | 3,4-Difluoro-phenyl | (−) | 50–55° |

Me = methyl; i-Pr = isopropyl
"core" indicates the configuration at the decahydro-isoquinoline: (+/−) is (4SR,4aSR,8aRS); (+) is (4R,4aR,8aS) and (−) is (4S,4aS,8aR)
"M.p." is the melting point of the free base, unless otherwise indicated
* : fumarate
** : dihydrochloride

What is claimed is:

1. A compound of formula I

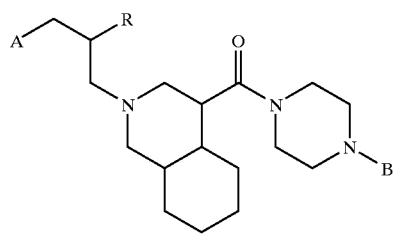

wherein R is hydrogen or $(C_{1-4})$alkyl and A and B, independently, are groups of formula (a), (b), (c), (d) or (e)

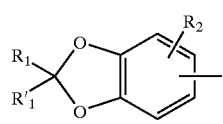

(a)

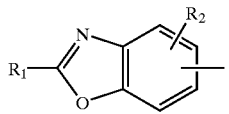

(b)

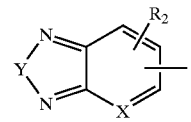

(c)

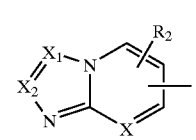

(d)

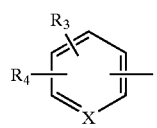

(e)

wherein

X, $X_1$ and $X_2$, independently, are —CR$_1$= or —N=

Y is —O—, —S—, —CH=CH— or —NH—

$R_1$ and $R'_1$, independently, are hydrogen, $(C_{1-4})$alkyl or $(C_{1-4})$alkoxy, $R_2$ is hydrogen, $(C_{1-4})$alkyl, $(C_{1-4})$alkoxy, $(C_{1-4})$alkoxycarbonyl) or halogen, and $R_3$ and $R_4$, independently, are halogen, nitro, cyano, trifluoromethyl, $(C_{1-4})$alkyl, $(C_{1-4})$alkoxy, $(C_{1-4})$alkoxycarbonyl or $(C_{1-4})$alkanoyl, in free base or acid addition salt form.

2. [4-(3,4-Difluoro-phenyl)-piperazin-1-yl]-{(4S,4aS,8aR)-2-[(S)-3-(6-methoxy-pyridin-3-yl)-2-methyl-propyl]-decahydro-isoquinolin-4-yl}-methanone in free base or acid addition salt form.

3. A process for the preparation of a compound of formula I as defined in claim 1, or a salt thereof, which includes the step of reacting a compound of formula II

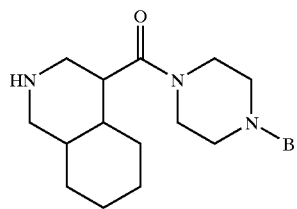

wherein B is as defined in claim 1, with a compound of formula III

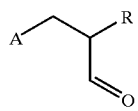

wherein A and R are as defined in claim 1, and recovering the thus obtained compound of formula I in free base or acid addition salt form.

4. A pharmaceutical composition comprising a compound of claim 1 in free base of pharmaceutically acceptable acid addition salt form, in association with a pharmaceutical carrier or diluent.

5. A method for the treatment of schizophrenia, depression, anxiety and bipolar disorders in a subject in need of such treatment, which comprises administering to such subject a therapeutically effective amount of a compound of claim 1 in free base or pharmaceutically acceptable acid addition salt form.

* * * * *